US00PP20590P3

(12) United States Plant Patent
Lentz

(10) Patent No.: US PP20,590 P3
(45) Date of Patent: Dec. 22, 2009

(54) APPLE TREE NAMED 'LENTZ JONAGOLD'

(50) Latin Name: *Malus domestica*
Varietal Denomination: Lentz Jonagold

(75) Inventor: William James Lentz, Honor, MI (US)

(73) Assignee: International Plant Management, Inc., Lawrence, MI (US)

( * ) Notice: Subject to any disclaimer, the term of this patent is extended or adjusted under 35 U.S.C. 154(b) by 0 days.

(21) Appl. No.: 12/152,993

(22) Filed: May 20, 2008

(65) Prior Publication Data

US 2009/0293163 P1 Nov. 26, 2009

(51) Int. Cl.
*A01H 5/00* (2006.01)

(52) U.S. Cl. ..... Plt./163

(58) Field of Classification Search ..... Plt./163
See application file for complete search history.

*Primary Examiner*—June Hwu

(57) ABSTRACT

A new and distinct variety of Jonagold apple tree, 'Lentz Jonagold,' originating as a limb mutation of the *Malus domestica* variety of 'Rubinstar' (U.S. Plant Pat. No. 7,167). This new variety is unique from its parent and other Jonagold cultivars in the early coloration of the fruit, the high percentage of coloration of the fruit and the red coloration of the leaf petiole and mid-vein.

4 Drawing Sheets

DESCRIPTION OF RELATED APPLICATIONS

The new variety, 'Lentz Jonagold' differs from its parent and other Jonagold varieties in the following characteristics:

A. The fruit of the new variety differs from 'Jonagored' (U.S. Plant Pat. No. 5,937), 'Romagold' (U.S. Plant Pat. No. 9,541), 'Excel' (U.S. Plant Pat. No. 10,314) and 'Daliguy' (U.S. Plant Pat. No. 6,148) in that the new variety has 95% to 100% red coloration as opposed to 'Jonagored' (U.S. Plant Pat. No. 5,937) which is red over yellow, 'Romagold' (U.S. Plant Pat. No. 9,541) which is 75% red, 'Excel' (U.S. Plant Pat. No. 10,314) which is 50% red and 'Daliguy' (U.S. Plant Pat. No. 6,148) which is half red.

The new variety differs from 'Schneica' (U.S. Plant Pat. No. 7,146), and 'Jored' (U.S. Plant Pat. No. 8,851), in the timing of the first coloration of the fruit. The new variety starts coloring six weeks ahead of the parent as opposed to 'Schneica' (U.S. Plant Pat. No. 7,146) which starts coloring 4 four to six weeks later, and 'Jored' (U.S. Plant Pat. No. 8,851) which starts coloring five days ahead.

The new variety differs from 'Jonagored Supra' (U.S. Plant Pat. No. 10,401) and 'Red Jonaprince' (U.S. Plant Pat. No. 11,112) in the timing of maturity of the fruit. The new variety ripens with the parent as opposed to 'Jonagored Supra' (U.S. Plant Pat. No. 10,401) which ripens 8 days earlier and 'Red Jonaprince' (U.S. Plant Pat. No. 11,112) which ripens four to five weeks earlier.

The new variety differs from 'Jonagold De Coster' (U.S. Plant Pat. No. 8,049) in the coloration of the petiole and leaf veins. 'Jonagold De Coster' (U.S. Plant Pat. No. 8,049) has green leaf mid-veins and does not mention the petioles. The new variety has dark red leaf petioles and leaf mid-veins.

B. The new variety differs from its parent in that it starts coloring six weeks earlier than the parent with 95% to 100% red coloration as opposed to 'Rubinstar' (U.S. Plant Pat. No. 7,590) which exhibits 70% to 90% red coloration. The new variety also shows dark red coloration in the leaf petiole and mid-vein, as opposed to 'Rubinstar' (U.S. Plant Pat. No. 7,590) which has a green leaf petiole and mid-vein.

Latin name of the genus and species of the plant claimed: *Malus domestica.*

Variety denomination: 'Lentz Jonagold'.

BACKGROUND OF THE INVENTION

A new and distinct variety of Jonagold apple tree originating as a limb mutation of the *Malus domestica* variety of 'Rubinstar' (U.S. Plant Pat. No. 7,590) hereinafter referred to as 'Lentz Jonagold'. This new sport is unique from its parent because the fruit starts coloring 6 weeks earlier than the parent with 95% to 100% red coloration.

SUMMARY OF THE INVENTION

This new and distinct variety of Jonagold apple tree was discovered in 2005 as a limb mutation of 'Rubinstar' (U.S. Plant Pat. No. 7,590), in an orchard planted in 1995. The new variety was noticed because the fruit started coloring in early August, six weeks ahead of the parent.

Observations during the next two seasons confirmed that the fruit starts coloring six weeks earlier than the parent with 95% to 100% red coloration as opposed to 'Rubinstar' (U.S. Plant Pat. No. 7,590) which exhibits 70% to 90% red coloration. The new variety also shows red coloration in the leaf petiole and mid-vein, as opposed to 'Rubinstar' (U.S. Plant Pat. No. 7,590) which has a green leaf petiole and mid-vein.

In August of 2005, buds were taken from the original limb and trees for further testing were produced by cleft grafting onto existing apple trees in Frankfort, Mich. In August of 2006, buds were taken from the original limb and were budded onto M9 337 rootstock (an unpatented selection) using the chip budding method of propagation. This process took place in Brentwood, Calif. Brentwood, Calif. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained at in Frankfort, Mich.

FIG. 1 illustrated the fruit of the new variety.

FIG. 2 illustrates the original tree with the new variety on the left and the parent 'Rubinstar' (U.S. Plant Pat. No. 7,590) on the right, on Sep. 16, 2007; three weeks before maturity; showing the early coloring of the new variety.

FIG. 3 illustrates a section of the fruit of the new variety at maturity.

FIG. 4 illustrates the blossom and buds of the new variety.

DETAILED BOTANICAL DESCRIPTION

A detailed description of the 'Lentz Jonagold' cultivar follows using The Royal Horticultural Society of London Colour Chart, 1986 edition, for color identification except where general color terms are sufficient.

Parentage: A limb mutation of 'Rubinstar', (U.S. Plant Pat. No. 7590). Locality of the original discovery and observations is 4300 Mick Road, Frankfort, Mich. 49635.

Tree:

*Tree age.*—12 years.
*Size.*—Large, height 3 m, width 3 m.
*Vigor.*—Vigorous, yearly growth averages 1 m.
*Density.*—Medium.
*Form.*—Upright spreading.
*Production.*—Very productive, averaging 800 bushels per acre.
*Growth type.*—Non-spur.
*Bearing.*—Annual.

Trunk:

*Texture.*—Smooth.
*Trunk color.*—Grayed Green 197A.
*Lenticels.*—Length 2 mm, width 1 mm.
*Lenticel color.*—Grayed Green 196C.
*Lenticel density.*—3 to 4 per $cm^2$.
*Average trunk diameter* 20 mm above ground.—23 cm.

Branches:

3 *year old branch.*—22 mm in diameter, color Grayed Green 197C, angle to 4 year old branch 45° to 60°.
2 *year old branch.*—9 mm to 11 mm in diameter, length 26 cm, color Grayed Green 197A, angle to 3 year old branch 35° to 50°.
1 *year old branch.*—5 mm to 8 mm in diameter, length 25 cm, color Grayed Purple 183A; lenticels round, very small, 0.01 mm in diameter, color Green-White 157A; angle to 2 year old branch 35° to 50°.

Leaves:

*Size.*—Length 12 mm, width 7 mm.
*Form.*—Broadly ovate.
*Base.*—Rounded.
*Apex.*—Broadly acute.
*Upper surface pubescence.*—Finely pubescent.
*Lower pubescence.*—Finely pubescent.
*Upper surface color.*—Green 137A.
*Lower surface color.*—Green 138B.
*Venation.*—Pinnate, 10 to 12 veins, mainly alternate, color Green 138C with Green138B toward mid-vein.
*Mid-vein.*—Upper surface coloration of faint Red 46A from base to mid-leaf, lower surface coloration of Red 46A extending from base of leaf mid-leaf.
*Margin.*—serrate.
*Petiole length.*—30 mm.
*Petiole width.*—2 mm at attachment to leaf, 4 mm at abscission layer.
*Petiole upper surface color.*—Green 137A with Red 46A for the lower 75% of the leaf fading to Green 137B to tip.
*Petiole lower surface color.*—Green 145C with Red 46A at base to mid-leaf fading to green 137C to tip.
*Petiole groove.*—None observed.
*Stipules.*—Very fine, at the base of the petiole on almost all leaves.
*Stipule length.*—10 mm.
*Stipule width.*—1 mm to 1.5 mm.
*Stipule color.*—Green 137A.
*Leaf glands.*—None observed.

Leaf buds:

*Length.*—5 mm.
*Width.*—5 mm.
*Color.*—Yellow-Green 145C.
*Placement on branch.*—Tightly applied.
*Internode distance.*—20 mm.

Spurs: Present on 2 year and older wood.

*Length.*—10 mm to 12 mm.
*Width.*—5 mm to 6 mm.
*Color.*—Grayed Purple 185A.

Bloom period: 7 days to 10 days depending on temperature and weather conditions.

Bloom timing: Mid-season

Pollination requirements: Viable pollen from another fertile variety blooming in the same time period such as Granny Smith (an unpatented selection), Honeycrisp, (U.S. Plant Pat. No. 7,197) or Indian Summer Crab apple (an unpatented selection).

Presentation: Showy.

Fragrance: Faint.

Fertility: Sterile.

Pollen: Sparse.

Flowers at popcorn stage:

*Pedicle.*—Length 42 mm, diameter 2 mm.
*Pedicel color.*—Green 138D.
*Bud.*—Length 10 mm, width 11 mm, shape, round.
*Bud color.*—Red Purple 64B on exposed surfaces with White 155D on covered surfaces.

Flowers at full bloom:

*Corolla diameter.*—50 mm.
*Numbers of flowers per cluster.*—5.
*Petals.*—Arrangement: 5 in number, length 23 mm, width 14 mm, separate. Color: adaxial: White 155D with a slight blush of Red Purple 64D. Abaxial: White 155D with blush of Red Purple 64D. Shape: elongated round with edged slightly curved inward, apex round, base rounded with point at junction to the receptacle. Texture: soft.
*Receptacle.*—Length 3 mm, width 2 mm, color Green 138D.
*Pedicel.*—Length 15 mm, width 4 mm, color Green 138D.
*Sepals.*—5 in number, length 9 mm, width 4 mm, pubescent, Color Green 138D with Green 138A at tip and edges.
*Stamens.*—21 to 25 in number, color White 155A.
*Anthers.*—Length 2 mm, width 1 mm, Color Yellow Orange 14B.
*Pistil.*—Held slightly lower than anthers in a majority of blossoms.
*Ovary.*—Length 9 mm, width 2 mm, color Yellow Green 145C, pubescent. Style: length 3 mm, width 0.1 mm, color Yellow Green 145C. Stigma: length 0.1 mm, width 0.1 mm, color Yellow Green 145B.

Fruit:

*Maturity when described.*—Firm ripe.

*Flesh firmness at maturity.*—16.3 to 18.8 pounds.

*Starch at maturity.*—5.0 to 7.5 (index of to 1 to 8).

*Brix at maturity.*—14.5 to 15%.

*Internal ethylene concentration at maturity.*—0.2 ppm.

*Date of picking.*—October 5, in Frankfort, Benzie County, Mich., generally harvested in one picking.

*Size.*—Axial diameter 85 mm, transverse diameter 90 mm.

*Fruit weight (firm ripe).*—270 to 300 g.

*Form.*—Uniform, symmetrical, regular, oblong-conical.

*Cavity.*—Acuminate, depth 12 mm, width 20 mm.

*Basin.*—Symmetrical, abrupt at base, wide, depth, 5 mm, width 20 mm.

*Calyx.*—Open, segments persistent, recurved, outer and inner surfaces pubescent.

Skin:

*Thickness.*—Thin.

*Texture.*—Smooth, medium glossy.

*Bloom.*—Medium to heavy.

*Tendency to crack.*—Slight.

*Lenticels.*—Round 0.5 cm in diameter, 2 to 3 per $cm^2$ color Yellow 10 D.

*Color.*—Solid 95% to 100% Red Purple 59 A with wide blotchy stripe of Red 53 A.

*Ground color.*—Yellow-Green 151 D.

Flesh:

*Aroma.*—Sweet, aromatic.

*Color.*—Yellow 11 D.

*Texture.*—Firm, tender, fine, crisp.

*Eating quality.*—Best.

Core:

*Bundle area.*—Medium to ovate, cordate, symmetrical at base.

*Bundle.*—Inconspicuous, green, alternate above stamens.

*Carpillary area.*—Distinct, medium size.

*Calyx tube.*—Funnel shaped, open.

*Depth of tube to shoulder.*—15 mm.

*Styles.*—Distinct, pubescent.

*Stamens.*—One distinct whorl, small.

*Axillary cavity.*—Wanting.

*Locules.*—Closed.

*Seed cells.*—Walls thin, tough, length 11 mm, width 6 mm.

*Longitudinal section.*—Ovate.

Seeds: Number perfect, 8 to 10.

*Number in one cell.*—1 to 2.

*Length.*—10 mm.

*Breadth.*—6 mm.

*Form.*—Ovate, non-tufted.

*Color.*—Grayed Purple 185A.

Stem:

*Length.*—32 mm to 35 mm.

*Width.*—3 mm to 5 mm.

*Color.*—Yellow Green 144A with slight coloration of Red 46A.

Use: Processing, fresh market, dessert.

Shipping quality: Good, subject to stem puncture.

Keeping quality: Excellent, 90 days to 120 days in common storage, 6 months in controlled atmosphere storage.

Tree winter hardiness: Average for an apple variety. Tree is hardy to −10° F. to −25° F.

Bud winter hardiness: −15° to −20 F., dependent on the stage of development of the bud.

Drought tolerance: Average for an apple variety. Normal requirements average ½ of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases.

I claim:

1. A new and distinct variety of Jonagold apple tree, *Malus domestica*, substantially as herein shown and described.

* * * * *

FIG. 1 'Lentz Jonagold'
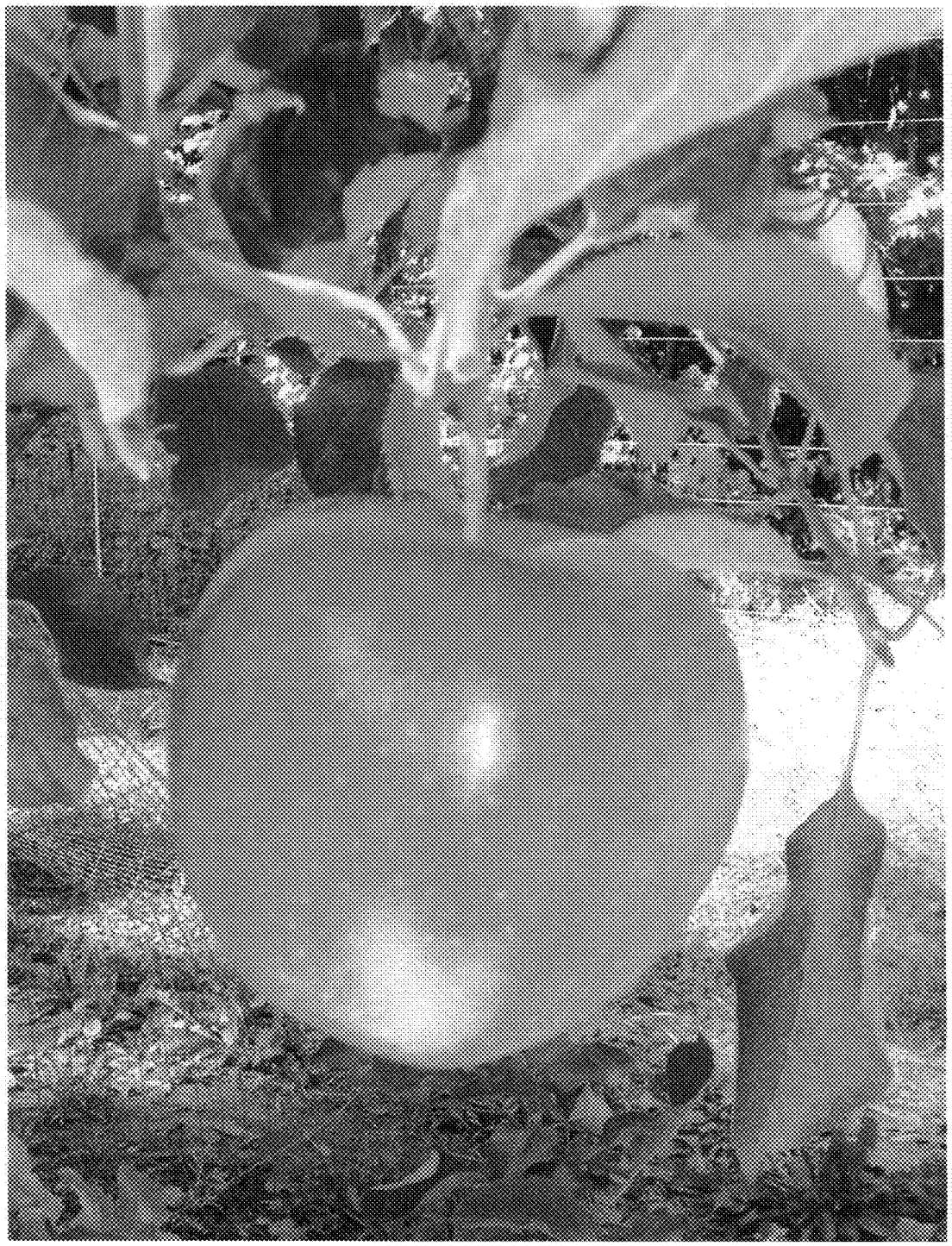

FIG. 2 'Lentz Jonagold'
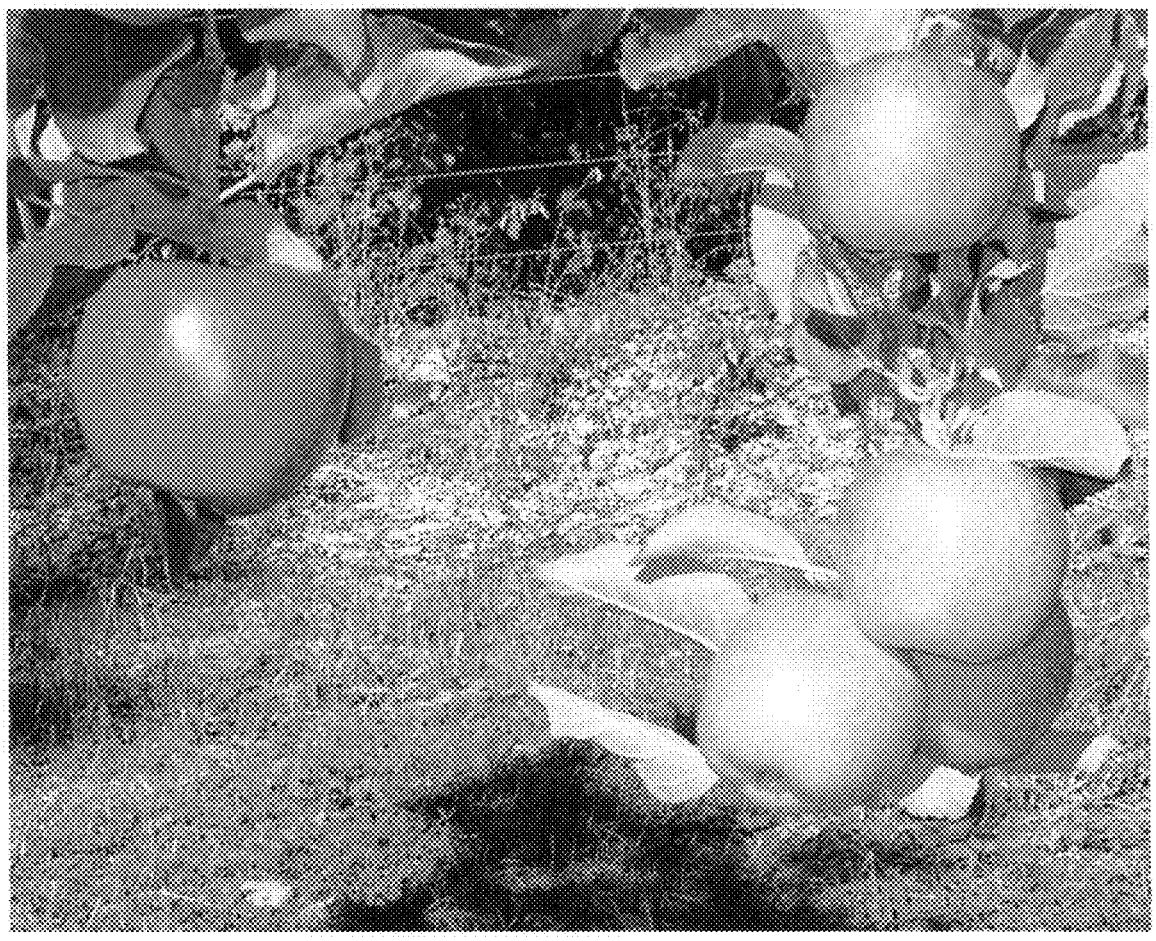

FIG. 3 'Lentz Jonagold'
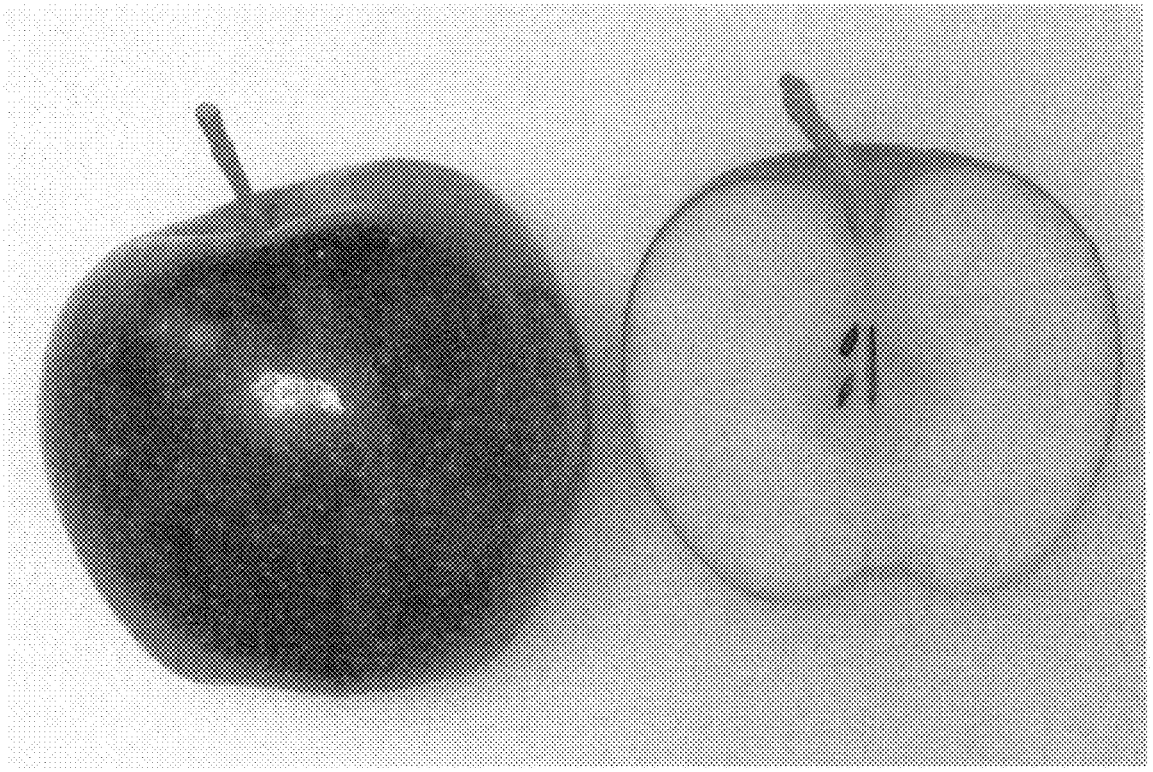

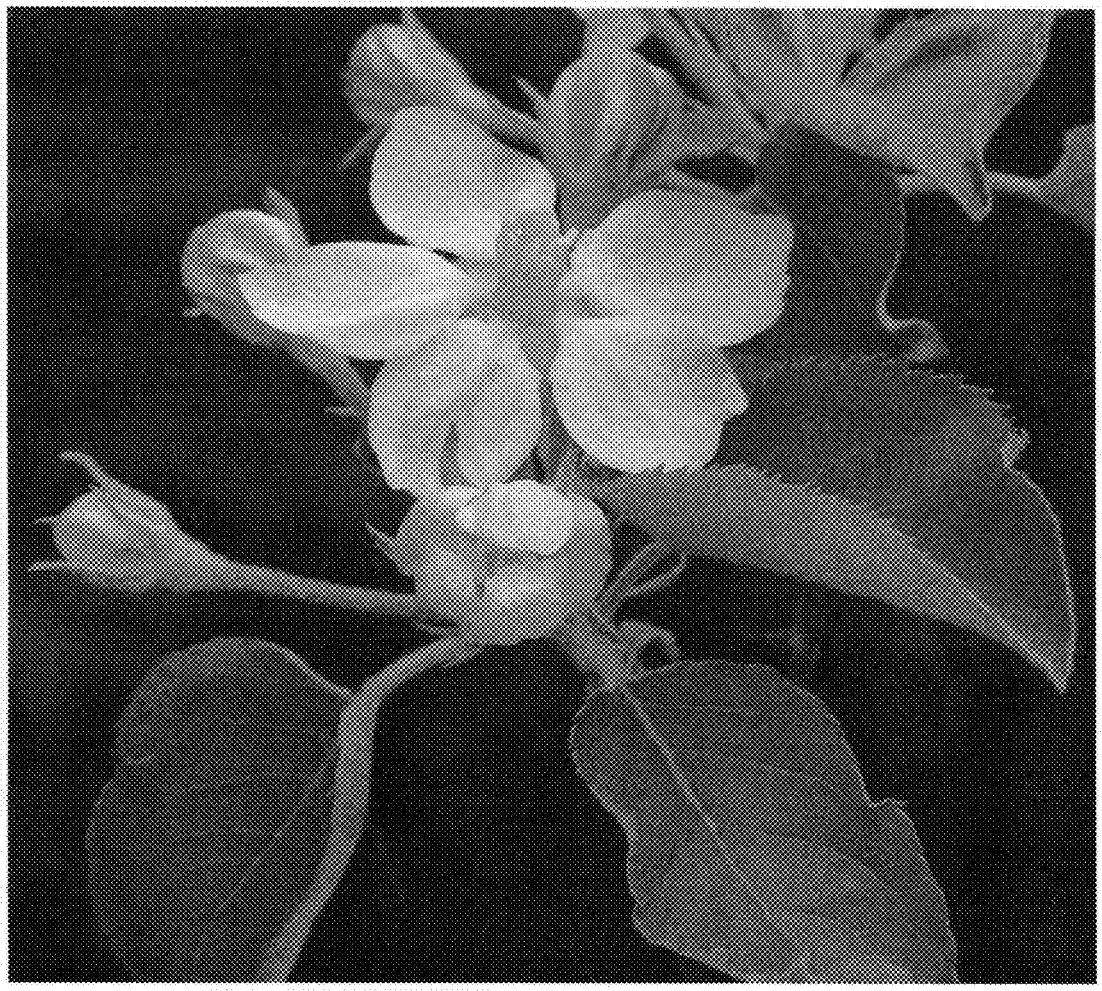

FIG. 4 'Lentz Jonagold'